United States Patent [19]

Amaral

[11] Patent Number: 5,181,563
[45] Date of Patent: Jan. 26, 1993

[54] ANATOMICALLY SHAPED ABSORBENT PAD

[75] Inventor: Everson Amaral, Sao Paulo, Brazil

[73] Assignee: McNeil-PPC, Inc., Milltown, N.J.

[21] Appl. No.: 453,215

[22] Filed: Dec. 14, 1989

Related U.S. Application Data

[63] Continuation of Ser. No. 336,623, Apr. 7, 1989, abandoned, which is a continuation of Ser. No. 26,362, Mar. 16, 1987, abandoned.

[51] Int. Cl.$^5$ ............................................. A61F 13/15
[52] U.S. Cl. ............................... 604/385.2; 604/378; 604/385.1
[58] Field of Search ............... 604/366, 370, 378, 379, 604/385.1, 385.2, 386, 387

[56] References Cited

U.S. PATENT DOCUMENTS

| | | | |
|---|---|---|---|
| Re. 31,922 | 6/1985 | Mesek et al. | 604/385.2 |
| 3,763,863 | 10/1973 | Mesek et al. | 604/385.2 |
| 3,860,003 | 1/1975 | Buell | 604/385.2 |
| 4,411,660 | 10/1983 | Dawn et al. | 604/396 |
| 4,515,595 | 5/1985 | Kievit et al. | 604/385.2 |
| 4,527,990 | 7/1985 | Sigl | 604/385.2 |
| 4,552,795 | 11/1985 | Hansen et al. | 604/385.2 |
| 4,573,987 | 3/1986 | Lamb, Jr. | 604/378 |
| 4,578,070 | 3/1986 | Holtman | 604/378 |
| 4,579,556 | 4/1986 | McFarland | 604/385.2 |
| 4,598,528 | 7/1986 | McFarland et al. | 604/385.2 |
| 4,636,209 | 1/1987 | Lassen | 604/378 |
| 4,639,949 | 2/1987 | Ales et al. | 2/400 |
| 4,640,859 | 2/1987 | Hansen et al. | 604/385.2 |
| 4,673,402 | 6/1987 | Weisman et al. | 604/368 |
| 4,681,577 | 7/1987 | Stern et al. | 604/378 |
| 4,701,177 | 10/1987 | Ellis et al. | 604/385.2 |

FOREIGN PATENT DOCUMENTS 0091412 3/1983 European Pat. Off.
2156681 2/1985 United Kingdom.

*Primary Examiner*—Allen J. Flanigan

[57] ABSTRACT

The invention refers to an anatomic absorbent which contrary to similar products exhibits dynamic and anatomic action, accompanying the movement of the body of the user and providing increased protection against leakage. The absorbent of the invention comprises an absorbent substrate (3) sandwiched between a permeable and an impermeable layer (1, 2) which are sealed to each other at least at the ends of the absorbent. On each side, at least along a part of its length, there is provided between the edges of said layers (1, 2) a strip (6) of heat-shrinking material in the contracted state, so that each side takes the form of a raised flap (4 and 5). Said layers are bonded to the strips (6) at a plurality of regions interspaced along the lengths of the strips, there being no continuous bond between the layers and those parts of the flaps which are provided with the strips.

6 Claims, 2 Drawing Sheets

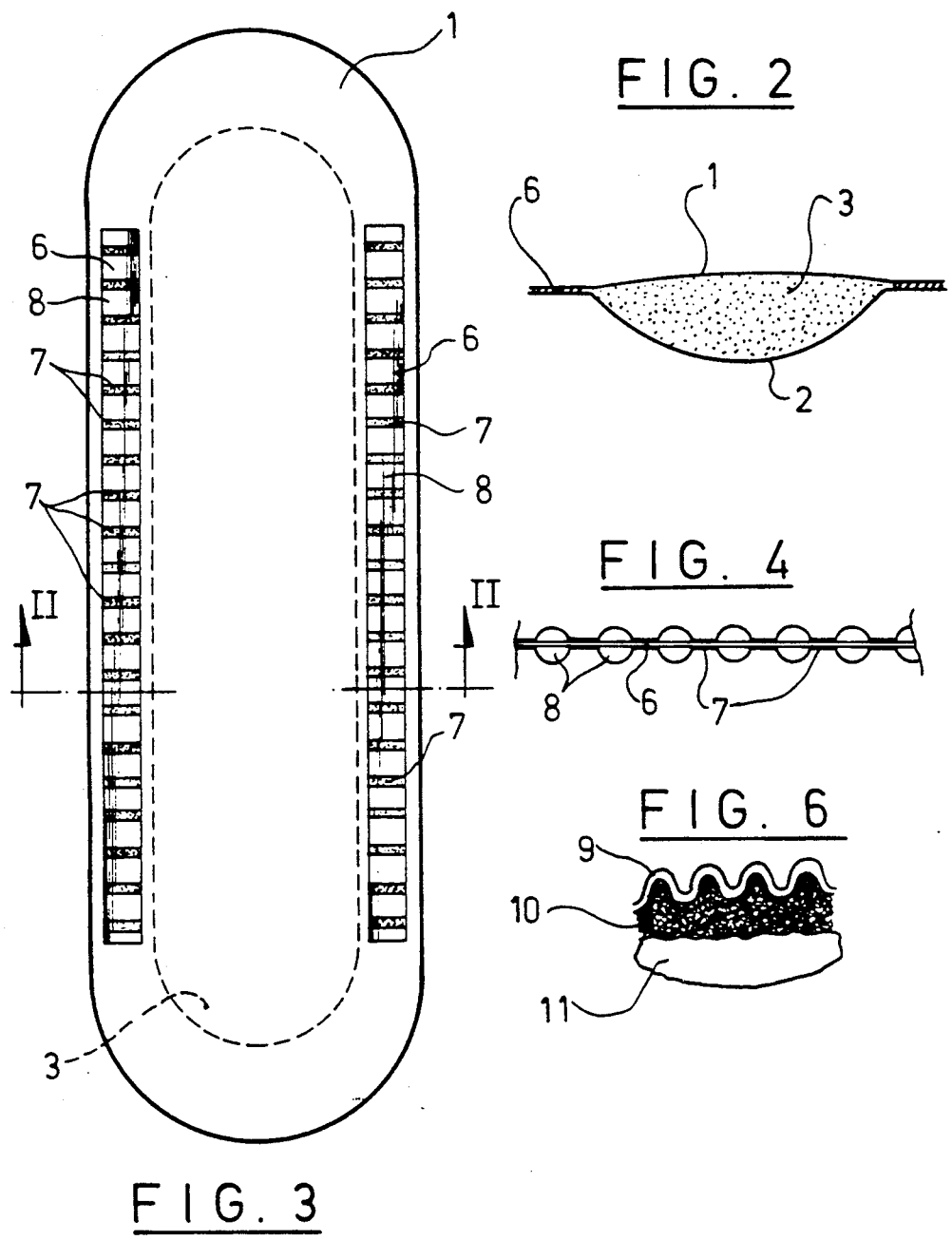
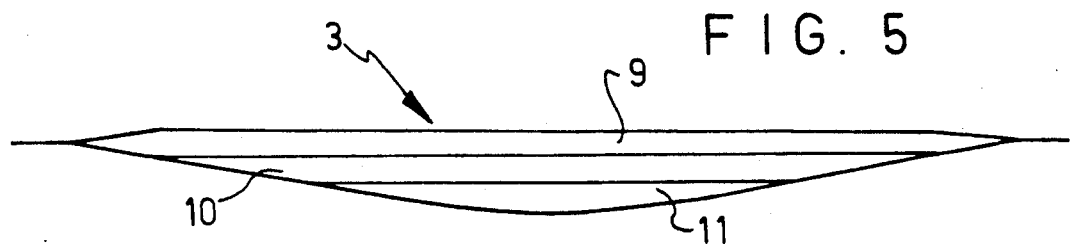

ANATOMICALLY SHAPED ABSORBENT PAD

This is a continuation of application Ser. No. 336,623, filed Apr. 7, 1989 now abandoned, which in turn was a continuation of application Ser. No. 026,362, filed Mar. 16, 1987 now abandoned.

The present invention refers to disposable hygienic absorbents for external use. The prior art has attempted to optimize the efficiency of such disposable products using static concepts in the design of the absorbent substrate, the shape of the pulp body and the improvement of the wrappings. More recently, modifications were proposed with a view to producing a product having an anatomic shape, examples thereof being the absorbents described in French Patent No. 2513115 and in Brazilian Patent Application No. PI-8500769. In the case of the French patent, the anatomic shape obtained by a longitudinal curve of the total product and a special shape on the upper absorbent substrate. The product of the Brazilian patent application on the other hand comprises an absorbent substrate sandwiched between an impermeable layer designed to be remote from the body of the user and a fluid permeable layer for surface contact in the perineal area of the user. The layers are joined to each other completely around the product along a line spaced inwardly from the peripheral edge thereof. In the central part of the side of the product and outside said sealing line, there is a length of elastic which forces the ends of the absorbent upwardly and towards each other, and the sides inwardly so as to form a cup-shaped profile.

The object of the above-mentioned patent application PI-8500769 is to make the absorbent product anatomic whereby it becomes more comfortable to use and less susceptible to leakage. In spite of this, two serious disadvantages have been observed.

Firstly, the shape is not truly anatomic, and could be called pseudo-anatomic, since the elastic strips do not permit flexion which suitably follow the natural movement of the body of the user. Consequently, only relative comfort is provided.

Secondly, the existence of the sealing line between the inner and outer layers which precisely follows the contour of the absorbent substrate and is disposed internally of the elastic strips, creates a non-absorbent strip. Thus when the fluid flow is excessive and there is not time for it to be absorbed by the absorbent substrate through the permeable layer, an accumulation of fluid is formed on the above-mentioned nonabsorbent strip. In such conditions, there is the risk of fluid leaking over the edges of the product or of producing a feeling of discomfort.

With respect to the first disadvantage mentioned above, it will be understood that the development was seeking an anatomic shape in the initial static conditions of use of the product, such shape, however, being lost in dynamic conditions.

The present invention has the purpose of overcoming, at least to a great extent, the above-mentioned disadvantages.

According to the invention, an elongate anatomic absorbent comprises an absorbent substrate sandwiched between a fluid impermeable layer designed to be remote from the body of the user, and a fluid permeable layer for surface contact in the perineal area of the user. These layers are sealed to each other at least at the ends of the absorbent and the sides of the absorbent are provided with elastic means to produce a curved anatomic outline, the absorbent being characterized by the fact that each said elastic means comprises a strip of heat-shrinkable material in the contracted state, so that the sides of the absorbent assume the shape of flaps lifted with relation to horizontal, said layers being adhered to the strips at a plurality of regions inter-spaced along the lengths of strips, the seal between the layers not being continuous in those parts of their flaps which are provided with the strips.

Preferably the absorbent substrate comprises a first layer in contact with the permeable layer, which has characteristics of resilience; a second central layer serving as a fluid reservoir; and a third layer in contact with the impermeable layer, said three layers of the substrate being successively shorter.

The invention is, therefore, based on the use of heat-shrinkable type elastic material at the edges of the products between the permeable and impermeable layers, so that, after heat-shrinkage, the product acquires a pseudo-anatomic shape. The characteristics of the heat-shrinkable material are considerably different from those of common elastic, as used in the prior art, since elastic forces are uniformly distributed along the length and across the width of the shrinkable strips. As a result, the sides of the absorbent product take the form of upwardly and inwardly turned slightly elastic flaps, which anatomically accompany the movements of the body of the user.

Apart from this, the fact that the bond between the permeable and impermeable layers and the strips of heat-shrinkable material is discontinuous along the strips, results in a slight wrinkling and raising of the flaps along the sides of the absorbent substrate after the heat-shrinkage, which further increases comfort and moreover permits any excess fluid not immediately absorbed and tending to collect in the channel defined around the periphery of the absorbent substrate, to be absorbed in this region because of the absence of continuous sealing. If liquid collects in the wrinkled area, it may for the same reason penetrate the permeable layer and flow downwards to be absorbed by the substrate.

The invention will now be described in greater details by way of example, with reference to the drawings, in which:

FIG. 1b is a schematic representation of the cross-section of the absorbent of FIG. 1a;

FIG. 2 is a cross-section of the absorbent of FIG. 1 taken along the line 2—2 of FIG. 3;

FIG. 3 is a top view of the product prior to the heat-shrinkage operation;

FIG. 4 is a detail of the wrinkling of one side flap after the heat-shrinkage operation;

FIG. 5 is a diagramic representation of a longitudinal section of the absorbent substrate; and FIG. 6 is a detail of such substrate.

Figure 1A:
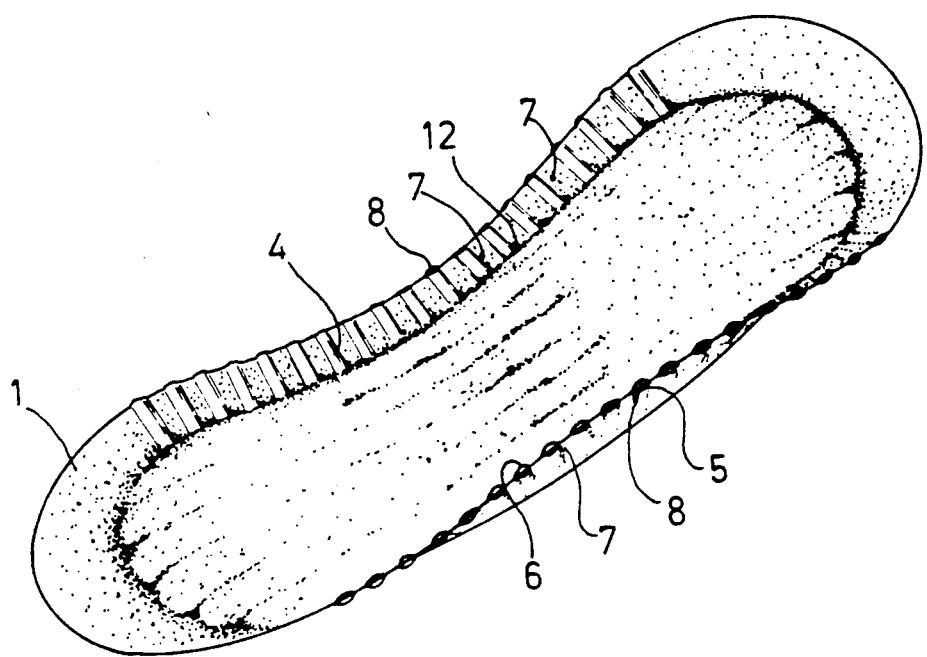
FIG. 1a is a perspective view of an anatomic absorbent manufactured in accordance with the present invention.
Figure 1B:
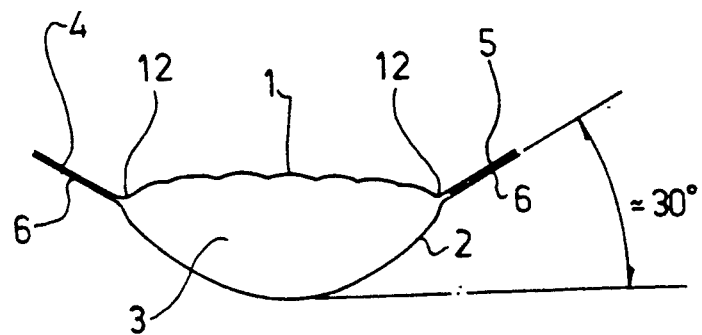

Referring now to FIGS. 1a and 1b, an anatomic absorbent according to the present invention comprises a fluid permeable layer 1 designed for surface contact with the perineal area of the user; a fluid impermeable layer 2, to be used remote from the body of the user; and sandwiched therebetween, ab absorbent substrate 3.

The absorbent has an elongate shape whose edges laterally of absorbent substrate 3 define flaps 4 and 5 which are raised substantially to continue the bottom profile of the product. Each of the side flaps 4 and 5 comprises not only the two layers 1 and 2, but also sandwiched therebetween along approximately 60% of the length of the product, a heat-shrinkable elastic strip 6 in a contracted state. This elastic strip is bonded to the two layers 1 and 2 along spaced parallel transverse lines, distributed along its length, to produce the wrinkling of the respective flap 4 or 5.

As can be seen from FIG. 1b, each flap 4 and 5 is raised by the action of the respective strip 6 to define an angle of approximately 30° to the horizontal, which can vary from 10° to about 90°. Said angle as well as the angle of the curve of the bottom surface of the product in the longitudinal direction are not critical, but a curve in the two directions mentioned are necessary to provide the product with its anatomic shape. Moreover, the elasticity provided by flaps 4 and 5 along the sides of the product ensures that the product is always resiliently and anatomically adaptable to the movements of the user.

Considering now FIG. 3, the product is shown in a top view in a stage of its manufacture immediately prior to the heat-shrinkage operation. Therefore, substrate 1 is visible and therethrough the absorbent substrate 3 and the two heat-shrinkable strips 6. Manufacture may then be completed by a heat-crimping machine at a temperature of 80°-100° C., preferably 90° C., which applies heat and pressure to the regions indicated by dotted lines 7 in FIG. 3. The effect of this operation is to create bonds between each strip 6 and layers 1 and 2 along lines 7 and furthermore provoke heat-shrinkage of strips 6 resulting in the contraction and wrinkling of the side edges of the product to form flaps 4 and 5. This wrinkling may be seen in FIG. 4, which also shows the bonding lines 7 between the two layers 1 and 2 and one of the strips 6, leaving non-bonded free areas 8.

Strips 6 may be made from any suitable heat-shrinkable material, for example PVC (polyvinyl chloride), 5 EPDM (ethylene-propylene-diene monomer) or any other similar material.

It will also be observed that the permeable and impermeable layers 1 and 2 are made from pieces of material cut to have straight parallel sides. In spite of this, it could be advantageous for their sides to be slightly concave.

FIG. 5 shows a longitudinal section of absorbent substrate 3 which comprises three layers 9, 10 and 11. The absorbent layer 9 arrange to be in contact with the permeable layer 1, has resilient properties provided by corrugations and embossments.

FIG. 6 shows layer 9 corrugated longitudinally of the product. The intermediate absorbent layer 10 is that which actuates as the liquid reservoir and it may or may not contain super absorbent material. The third layer 11, arranged to contact the impermeable layer of the product, actuates as a shape regulator transmitting sensorial characteristics and masking the fluids stored in layer 10, for example by application of liquid repellent, such as PERSISTOL ® commercialized by BASF.

As can be seen from FIG. 5, the three layers 9, 10 and 11 are gradually and successively shorter, to collaborate in the obtention of the anatomic shape of the final product.

As seen from FIG. 5, the layers 9, 10 and 11 can consist of cellulose fibres or synthetic textile fibres such as rayon, polyester, polypropylene and other fibres. In the case of an intermediate layer 10 made of super absorbent material, said material can be sodium polymetacrylate or any other suitable super absorbent material.

As already mentioned, the absorbent of the present invention has side flaps which, due to the heat-shrinkable strips 6, are raised and have an inherent elasticity which permits them to allow the natural movement of the body of the user, that is to say, permits the product to have an anatomic dynamic action.

Apart from this, any excess of fluid which is not immediately absorbed through the central part of permeable layer 1 and which tends to accumulate in channels 12 (see FIG. 1a) formed between, on the one hand the inner edges of flaps 4 and 5, and, on the other hand, the main body of the product, is still in contact with a permeable area, in communication with the absorbent substrate 3 due to the absence of a continuous bond line in this region. Experiments have shown that with this configuration the leakage index is lowered by at least 25% when compared with conventional products presently on the market.

It will be understood that the above description is directed to a preferred embodiment of the invention, and that various alterations are possible. It is preferred that the length of the heat-shrinkable strip 6 be approximately 60% of the length of the product. However, said strips may be shorter or longer although it is not advisable that they be less than 40% or greater than 80% of such length. Equally, the manner of effecting the bond between strips 6 and layers 1 and 2 may be varied provided that a continuous bond line is not produced. This and other other modifications are clearly within basic concept of the invention which should be limited only by the scope of the following claims.

I claim:

1. An elongated anatomic absorbent comprising an absorbent substrate having longitudinal edges along the length of the substrate and transverse ends, sandwiched between a fluid impermeable layer designed to be remote from the body of the user and a fluid permeable layer for surface contact in the perineal area of the user, said layers being bonded to each other at least at the ends of the absorbent, and the longitudinal edges of the absorbent having elastic means which provide it with an anatomic curved profile along the perineal area of the user, wherein said elastic means comprises a strip of heat-shrinkable material in the contracted state, so that the longitudinal edges of the absorbent are raised with relation to the horizontal, said layers being intermittently bonded to the elastic means at a plurality of regions interspaced along the lengths of the elastic means, the bond between the layers not being continuous in those parts of the side flaps which are provided with the elastic means such that the discontinuous bonds in the parts of the side flaps which are provided with the elastic means permit body fluid which would otherwise overflow the longitudinal edges and cause absorbent failure to flow directly to the absorbent substrate without substantial leakage.

2. An anatomic absorbent according to claim 1, wherein the length of each strip of heat-shrinkable material covers from 40 to 80% of the length of the longitudinal edge of the absorbent.

3. An anatomic absorbent according to claim 2, wherein the length of each strip of heat-shrinkable material is approximately 60% of the length of the longitudinal edge of the absorbent.

4. An anatomic absorbent according to claim 1 wherein each of said layers is made from pieces of material having straight parallel longitudinal edges.

5. An anatomic absorbent according to claim 1 wherein said absorbent substrate comprises a first layer in contact with said permeable layer, having resilient characteristics; a second central layer serving as a fluid reservoir; and a third layer in contact with the impermeable layer, said three layers of the substrate being successively shorter.

6. An anatomic absorbent according to claim 5, characterized in that said second layer of the absorbent substrate includes superabsorbent material.

* * * * *